US009119641B2

(12) United States Patent
Windolf et al.

(10) Patent No.: US 9,119,641 B2
(45) Date of Patent: Sep. 1, 2015

(54) DEVICE FOR MANIPULATING A BONE OR BONE FRAGMENT OR A SURGICAL INSTRUMENT, TOOL OR IMPLANT AND A METHOD FOR POSITIONING SUCH A DEVICE

(75) Inventors: Markus Windolf, Davos (CH); Christoph Martin Noetzli, Davos Platz (CH)

(73) Assignee: AO TECHNOLOGY AG, Chur (CH)

( * ) Notice: Subject to any disclaimer, the term of this patent is extended or adjusted under 35 U.S.C. 154(b) by 156 days.

(21) Appl. No.: 13/061,989

(22) PCT Filed: Sep. 2, 2009

(86) PCT No.: PCT/CH2009/000295
§ 371 (c)(1),
(2), (4) Date: Mar. 3, 2011

(87) PCT Pub. No.: WO2010/025575
PCT Pub. Date: Mar. 11, 2010

(65) Prior Publication Data
US 2011/0166447 A1    Jul. 7, 2011

(30) Foreign Application Priority Data
Sep. 3, 2008  (WO) ................ PCT/CH2008/000366

(51) Int. Cl.
*A61B 17/17* (2006.01)
*A61B 17/88* (2006.01)
(Continued)

(52) U.S. Cl.
CPC ............. *A61B 17/17* (2013.01); *A61B 17/8866* (2013.01); *A61B 19/20* (2013.01);
(Continued)

(58) Field of Classification Search
CPC ............... A61B 17/17; A61B 17/8866; A61B 17/1703; A61B 17/1725; A61B 17/3403; A61B 19/20; A61B 19/54; A61B 2019/5238; A61B 2019/5466; G01B 5/0002
USPC ............................................. 600/426; 606/97
See application file for complete search history.

(56) References Cited

U.S. PATENT DOCUMENTS 5,411,503 A * 5/1995 Hollstien et al. ............ 606/86 R
6,751,361 B1   6/2004 Wagman
(Continued)

FOREIGN PATENT DOCUMENTS

WO   2005/000129 A1   1/2005
WO   2007/056458 A2   5/2007
(Continued)

OTHER PUBLICATIONS

Neatpisarnvanit et al. "Intramedullary Nail Distal Hole Axis Estimation using Blob Analysis and Hough Transform." 2006 IEEE Conference on Robotics, Automation and Mechatronics. Jun. 1-3, 2006.*
(Continued)

*Primary Examiner* — Long V Le
*Assistant Examiner* — Colin T Sakamoto
(74) *Attorney, Agent, or Firm* — Rankin, Hill & Clark LLP

(57) ABSTRACT

A device and a method for guiding an instrument, tool or implant with respect to a three-dimensional body. The device includes a rod shaped member with a central axis, a rear end, a front end and a length L2. A first targeting element is fixed to the rod shaped member coaxially to the central axis. The first targeting element has a first center, and is arranged on the rod shaped member with the first center at a distance A1>0 from the rear end. A second targeting element with a second center is fixed to the rod shaped member coaxially to the central axis with the second center at a distance A2<A1 from the rear end. The first targeting element has a diameter $D_K$ measured orthogonal to the central axis of a minimum of 10 mm.

18 Claims, 5 Drawing Sheets

(51) Int. Cl.
  *G01B 5/00* (2006.01)
  *A61B 19/00* (2006.01)
  *A61B 17/34* (2006.01)

(52) U.S. Cl.
  CPC .......... *G01B 5/0002* (2013.01); *A61B 17/1703* (2013.01); *A61B 17/1725* (2013.01); *A61B 17/3403* (2013.01); *A61B 19/54* (2013.01); *A61B 2019/5238* (2013.01); *A61B 2019/5466* (2013.01)

(56) References Cited

U.S. PATENT DOCUMENTS

| | | | |
|---|---|---|---|
| 7,074,225 B2* | 7/2006 | Kimura | 606/97 |
| 7,175,631 B2* | 2/2007 | Wilson et al. | 606/97 |
| 8,046,054 B2* | 10/2011 | Kim et al. | 600/427 |
| 8,118,818 B2* | 2/2012 | Zheng et al. | 606/130 |
| 8,231,629 B2* | 7/2012 | Lerner et al. | 606/97 |
| 2002/0198451 A1* | 12/2002 | Carson | 600/426 |
| 2004/0030245 A1* | 2/2004 | Noble et al. | 600/426 |
| 2004/0143184 A1 | 7/2004 | Kienzle, III | |
| 2005/0027304 A1 | 2/2005 | Leloup et al. | |
| 2005/0080328 A1* | 4/2005 | Vass et al. | 600/426 |
| 2005/0251139 A1 | 11/2005 | Roh | |
| 2006/0084867 A1 | 4/2006 | Tremblay et al. | |
| 2006/0098851 A1* | 5/2006 | Shoham et al. | 382/128 |
| 2007/0270851 A1* | 11/2007 | Erickson et al. | 606/69 |
| 2010/0023065 A1* | 1/2010 | Welch et al. | 606/86 R |

FOREIGN PATENT DOCUMENTS

| | | |
|---|---|---|
| WO | 2008/019510 A1 | 2/2008 |
| WO | WO 2008071014 A1 * | 6/2008 |

OTHER PUBLICATIONS

Cho et al. Foundations of Medical Imaging. 1993. John Wiley & Sons, Inc. pp. 97-100.*

Zimmer(R). "ITST(TM) lntertrochanteric/Subtrochanteric Fixation System" product brochure. Revision 3. 2006.*

Murphy et al., "Image-Guided Radiosurgery for the Spine and Pancreas". Computer Aided Surgery 5: 278-288 (2000).*

* cited by examiner

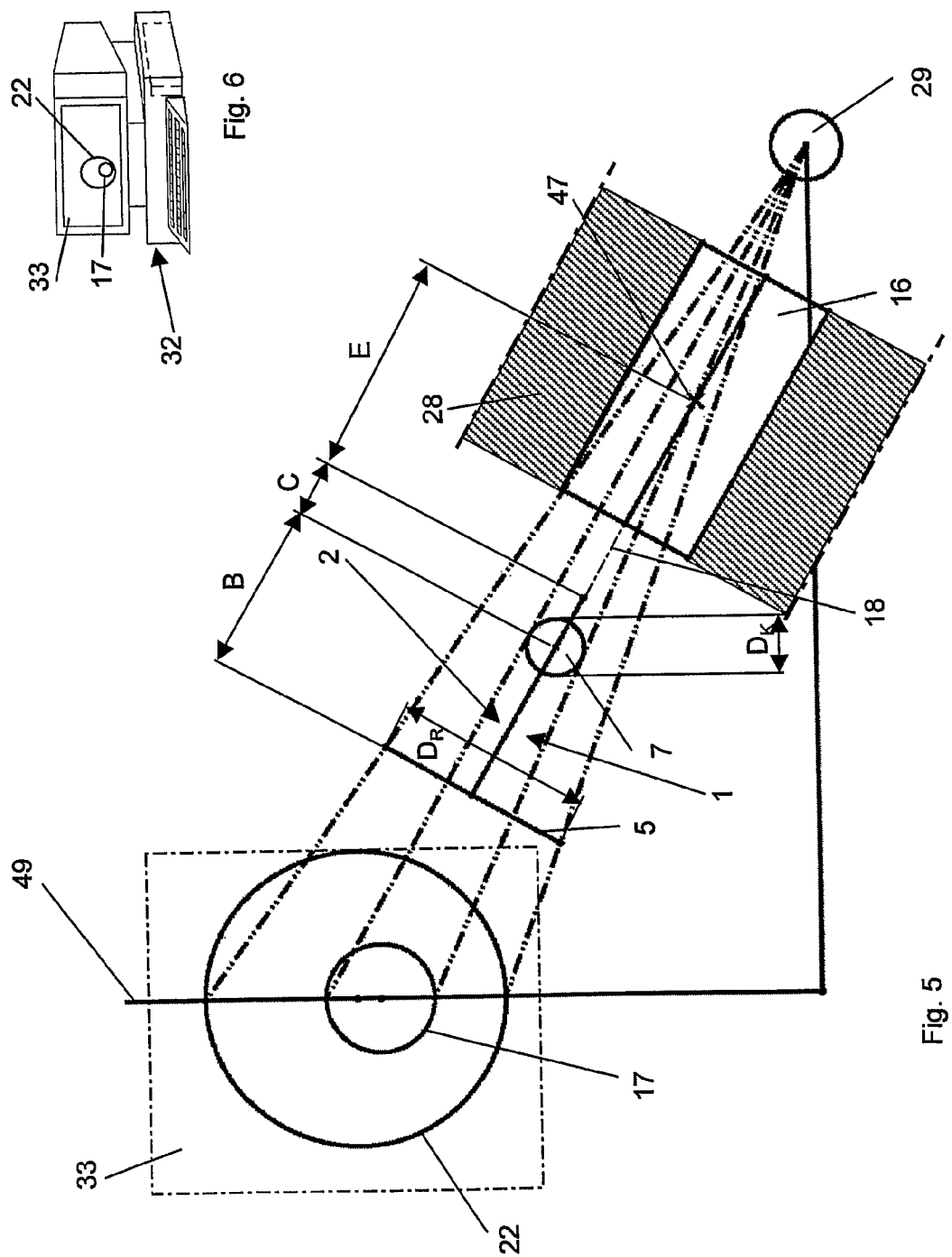

DEVICE FOR MANIPULATING A BONE OR BONE FRAGMENT OR A SURGICAL INSTRUMENT, TOOL OR IMPLANT AND A METHOD FOR POSITIONING SUCH A DEVICE

The invention relates to a device for manipulating a bone or bone fragment or a surgical instrument, tool or implant according to the preamble of claim 1 and to a method for positioning the device, instrument or tool in a desired position with respect to a three-dimensional body according to the preamble of claim 9.

FIELD OF THE INVENTION

In various technical applications where a work piece or other object has to be machined or processed it is often necessary to determine its location and/or angular orientation with regard to a known system of coordinates. Often such objects are visually inaccessible or their position and angular orientation cannot directly be determined by usual measurement methods.

Such technical applications include for example:
1. to guide any type of tool in a predetermined direction with respect to a work piece or other object for further machining or processing of said work piece or other object;
2. measurement of alignment of a printed circuit board and register subsequent drilling of a bore hole;
3. measurement of layer displacement in a multilayer board or panel for e.g. quality control;
4. measurement of distortion and/or rotation of a single or multi-layer work piece or other object in order to recover a desired shape or orientation or in order to align a robotic arm in e.g. a robotic assembly system;
5. determination of the alignment of objects that may not be mechanically constrained in a predetermined location or angular orientation, for example
    locating and manipulating of a cardiac pacemaker, e.g. tightening or loosening of a screw;
    fixation, i.e. interlocking of a shaft of an endoprosthesis (e.g. shaft of femur component).
6. handling or manipulating of a work piece or other object with exact knowledge of its position and orientation.

DESCRIPTION OF THE PRIOR ART

A machine vision system for object location and inspection is known from U.S. Pat. No. 6,751,361 WAGMAN. This known system comprises a single non-rotationally symmetric fiducial mark which is placed at a predetermined location on the object, a vision tool to process an image of the object obtained with a camera in order to locate the fiducial mark in the image and to determine its location and angular orientation with respect to a fixed system of coordinates and using the location and angular orientation of the fiducial mark to calculate the position of the object with respect to the fixed system of coordinates. The image processing system of this known device uses a series of images which are provided to the vision tool that locates fiducial marks on objects in the image. The use of a series of images can however be disadvantageous in case of an X-ray image acquisition device.

From US-A 2005/0251139 ROH a set of screw preparation instruments is known which includes a ball tipped measuring probe with a cannulated metallic depth gauge ruler arranged slideably on said probe. The measurement of the length of the screw path is determined using the base of the ball-tipped probe so that in case of a bore hole extending through a pedicle said base of the ball-tipped probe abuts the countersurface of the pedicle. The measuring probe is provided with a radiolucent targeting handle marked with a targeting guide oriented along the central axis of the probe shaft in order to confirm proper alignment of the measuring probe along the working axis.

SUMMARY OF THE INVENTION

It is an object of the present invention to provide a simple device and a method for performing a surgical manipulation or treatment of a three-dimensional body allowing to reduce the X-ray exposure of the patient and the operator and at the same time avoid the usage of costly and time consuming navigation equipment.

The invention solves the posed problem with a device for manipulating a bone or bone fragment or a surgical instrument or tool displaying the features of claim 1 and a method for positioning the device in a desired position with respect to a three-dimensional body displaying the features of claim 9.

Due to the device according to the invention the following advantages can be achieved:
  an intraoperative visual and manual positioning of the device is possible by using a fluoroscope. The diameter of the first targeting element is between 10 mm and 20 mm, preferably between 12 mm and 16. A typical diameter of the first targeting element is 14 mm. A minimum diameter of the first targeting element of 10 mm is reasonable since the method according to the invention is a visual method for positioning the device. A proper visual alignment of a targeting element requires a certain size of said targeting element. The first targeting element is then always intra-operatively visible at least partially in an X-ray image (fluoroscopic image) when it is moved into the area of the projected implant, e.g. the shaft of an endoprosthesis or a bone screw.

In a special embodiment said first targeting element has the form of a sphere or a disc or a ring. The advantage of a disc, e.g. a spherical layer or ring shaped first targeting element is that it can be placed close to the cortex of a bone. By this means a clear separation of the rotational and translational movement of the device can be achieved if the tip of the aiming device is specified as the center of rotation.

With a decreasing distance C between the center of the first targeting element and the front end of the device the translation is getting decoupled from the rotation when assuming that the center of rotation is the front end of the device. Ideally C→0.

The distance C between the center of the first targeting element and the front end of the aiming device can approach 0 with the above mentioned advantage in case of the first targeting element being disc or ring shaped. It is possible to place the first targeting element at a greater distance to the front end of the rod shaped member to avoid penetration of the first targeting element through the skin of the patient. The form of the first targeting element is configured in such manner that a circular projection area is achieved under varying angles of projection. The spherical configuration of the first targeting element has the advantage that the projection area is independent of the orientation of the aiming device. Further, since the aiming device has to be advanced in some cases through the soft tissue until the surface of the bone the curvature of a sphere is advantageous compared to the flat front surface of a disc.

In another embodiment the median cross-sectional area orthogonal to said central axis and containing said first centre of said sphere, disc or ring has a circular periphery with said diameter $D_K$.

In a further embodiment at least one of said first and second targeting elements, preferably said first targeting element has a spherical portion with a radius of curvature R1 directed towards said rear end of said rod shaped member and directed towards said front end a front portion with a radius of curvature R2 which is equal or greater than R1.

The spherical rear portion of said first targeting element has a radius of curvature R1 of minimum 5 mm. The first targeting element has a diameter $D_K=2*R1$. The front portion of said first targeting element has a radius of curvature R2 ranging from minimum R1 to infinite, i.e. a flat front portion. The front portion of said first targeting element is limited towards said front end of said rod shaped member by a plane extending orthogonal to said central axis and contacting said front end.

In various embodiments the first and second targeting elements can be two spherical elements, two elements each forming a reference frame or a combination thereof.

In another embodiment said rod shaped member has a length L2 measured in the direction of said central axis which is in a range between 40 mm and 120 mm, preferably between 45 mm and 90 mm.

In a further embodiment said device is an aiming device for guiding an instrument, tool or implant with respect to a three-dimensional body and wherein said rod shaped member is a tubular member with an external diameter $D_t$ and a central through bore for guiding an instrument, tool or implant.

In yet another embodiment at least one of said first and second targeting elements, preferably said second targeting element has an annular form with a circular central line with a diameter $D_R>D_K$ and lying in a plane perpendicular to said central axis. Said second targeting element is arranged in such manner that its circular central line is concentrical to said central axis.

Said annular targeting element can have the form of a reference frame defining a plane orthogonal to said central axis of said rod shaped member. The annular targeting element can be arranged in front of the spherical targeting element or behind the spherical targeting element.

Preferably, said second targeting element is a torus with a circular cross-section of radius $r_1$ orthogonal to said circular central line or a ring with a cross-section of a regular polygon, preferably a square with a side length $r_1$. For the present method which is a visual method the cross-section of the torus is of secondary relevance.

Said diameter $D_R$ of said circular central line is in a range between 30 mm and 100 mm, preferably between 40 mm and 60 mm. Typically the diameter $D_R$ is 50 mm.

Said radius or side length $r_1$ of said second targeting element is in a range between mm and 10 mm, preferably between 3 mm and 6 mm.

In a further embodiment said aiming device for guiding an instrument or tool with respect to a three-dimensional body comprises:

a tubular member with a central axis, an external diameter $D_t$, a central through bore for guiding a drill bit, a rear end and a front end both transverse to the central axis,
an annular targeting element which has a circular central line with a diameter $D_R>D_t$ and lying in a plane perpendicular to said central axis; said first targeting element being arranged such that its circular central line is concentrical to said central axis and at a distance A2>0 measured from said rear end towards said front end and being coupled to said tubular member by radiolucent means; and
a spherical targeting element which has a diameter $D_K$ and a center and which is fixed to said tubular member concentrically to said central axis so that said center of said spherical targeting element is at a distance B measured from said plane defined by said circular central line towards said front end and at a distance C>0 from said front end, and wherein $D_t<D_K<D_R$.

In another embodiment said device comprises at least two cylindrical or prismatical targets which are arranged parallel to each other and at an identical distance $A_{Target}$ from said central axis of said rod shaped member.

In still a further embodiment said second targeting element comprises a radiolucent means, preferably in the form of a radiolucent disc.

In another embodiment said at least two cylindrical or prismatical targets are integrated in said radiolucent means.

In again another embodiment said at least two cylindrical or prismatical targets are configured as hollow cylindrical targets.

Said first and second targeting element as well as said at least two cylindrical or prismatical targets consist of a radiopaque material.

In a further embodiment said aiming device comprises a handle.

The method according to the invention allows the following advantages:

an aiming device for guiding a tool or instrument can be aligned in a desired position with respect to a three-dimensional body by using a fluoroscope;
a target with a lower density than the surrounding material can be located. For instance, a cylindrical target can therefore be a cavity (communicating with the surface of a three-dimensional body or blind in the interior of the three-dimensional body) or the targets can be cylindrical objects like bars. In both cases it is possible to make these cylindrical targets visible with electromagnetic waves (e.g. X-rays) or acoustic waves (e.g. ultrasound); and
by locating one cylindrical target it is possible to position an object with regard to five degrees of freedom.
standard implants, bone fixation devices, e.g. standard bone screws available on the market can be used;
no sensors have to be affixed to the implants or bone fixation devices used;
the needed X-ray device (c-arm image intensifier) is available in the majority of clinics;
additional tracking devices and robots are not necessary;
modification of the implant is not necessary;
independency of the design of the bone fixation device or implant; and
useable for any application comprising an implant or a bone fixation device with a bore of known shape.

In a special embodiment said target has a lower density than the surrounding material of said three-dimensional body.

In a further embodiment said target is circular cylindrical with a diameter d and a height h. The target can such be a bore hole formed in a solid body.

The center of the target is the center of gravity of the target in case of a solid target or the center of gravity of a corresponding cylinder if the target is a bore hole in a solid body.

The term cylindrical target is used for a solid or a cavity bounded by a cylindrical surface produced by a straight line which moves in space without altering its direction along a closed curve limiting the base and top surfaces which are parallel and congruent relative to each other.

The term prismatical target is used for a solid or a cavity bounded by a prismatic surface produced by a straight line which moves in space without altering its direction along a polygon limiting the base and top surfaces which are parallel and congruent relative to each other.

In a special embodiment of the inventive method said positioning of said device is performed manually.

In a further embodiment said positioning of said device is performed by firstly aligning said first targeting element with said first targeting curve by translational movement of said device and by secondly aligning said second targeting element with said second targeting curve by rotational movement of said device.

Apart from the target curves tolerance ellipses or curves are depicted, which define a range for placement of the aiming device. This tolerance ellipses or curves are important since the positioning of the aiming device is performed freehandedly. By means of the tolerance ellipses or curves an estimation of the allowed deviations for positioning the aiming device can be achieved.

In another embodiment said image acquisition device features a central projection.

In yet another embodiment said image acquisition device includes an energy emitting source allowing an approximation as a punctiform energy source and with a central ray at a known position with regard to said image and wherein said target is circular cylindrical and that upon acquiring said single image the angulation range between the central ray and the longitudinal axis of said target is restricted in a way that a lens-shaped projection of said target is visible on said image.

In a further embodiment said numerical procedure essentially comprises the steps of:
- i) automatic detection of a lens-shaped projection of said target in said image and determination of the two points of intersection and the first and second apex of said lens-shaped projection of said target;
- ii) generating a virtual geometric representation of said target with said diameter d, said longitudinal axis, said centre and said height h;
- iii) determining the virtual projection points representing said two points of intersection and said first and second apex using said virtual geometric representation of said target; and
- iv) iterative determination of the position and orientation of said target by matching said virtual projection points of said virtual geometric representation of said target with said two points of intersection and said first and second apex.

The advantage of this embodiment is essentially to be seen therein that the present method of reconstructing a position of a target from projections of said target uses four points only for achieving a unique and robust spatial reconstruction from a single projection image. Only little calculation expenditure is necessary thus allowing a fast calculation procedure.

When a target with another shape than circular cylindrical is used the numerical method must be adapted accordingly.

Another embodiment comprises the step of:
- determining the position of at least two cylindrical targets in said three-dimensional body, wherein said targets are arranged with known position and orientation relative to each other; and
- determining the position and angular orientation of said three-dimensional body with respect to a fixed system of coordinates using said position and angular orientation of said at least two cylindrical targets by means of said computer.

By locating two cylindrical targets it is possible to unambiguously define the exact position and angular orientation of an object containing the two cylindrical targets (six degrees of freedom).

For a determination of the position and angular orientation of a non rotational symmetric target, e.g. a prismatic target one single target is sufficient.

The orientation of said first and second target is defined with respect to each other in such manner that said projections of said first and second target are visible in said single image.

In still a further embodiment the inventive method includes the additional steps of:
- I) fixing at least one target in or on each object which is relevant for said surgical operation;
- II) establishing a 3D representation of a relevant body portion of a patient by using a standard medical acquisition means;
- III) planning of the surgical procedure to be performed at said relevant body portion by using a computer and said 3D representation of the relevant body portion;
- IV) acquiring one single image with a projection of said at least one target by means of an image acquisition device with a projection plane;
- V) performing steps b) to f) of the inventive method; and
- VI) performing the planned surgical procedure by using said device according to the invention and said computer, wherein said step of:
fixing at least one target in or on each object which is relevant for said surgical operation can be performed before step IV) instead of before performing steps II) to III).

Objects relevant for said surgical operation can be one or more anatomical objects of a body portion of a patient, one or more relevant instruments, tools or implants used during performing the planned surgical procedure.

In another embodiment step IV) comprises:
- IV) acquiring one single image with a projection of all targets of at least one of said objects by means of an image acquisition device with a projection plane; and if not all targets of all objects are visible in said single image:
- repeat step IV) for further objects until the projection of all targets of each object are visible in one of said images.

According to the inventive method all targets fixed to one object must be visible in a single image.

In case of having more than one object and not all targets of all objects are visible in one single image further images for the other objects are acquired.

Standard medical acquisition means can be CT (computed tomography), MRI (magnetic resonance imaging) or 3D radiologic imaging. 3D radiologic imaging is preferred if a standard radiologic device (like a c-arm) is used for the described navigation method. This has the advantage that targets can already by placed prior to 3D imaging and are therefore already visible and accessible during planning.

The targets can be placed subcutaneously or above the skin, but need a rigid connection to the respective object.

Instead of using a single non rotational symmetric, e.g. prismatical target a marker element comprising a small plate with at least two cylindrical bores as targets can be used.

The step of performing surgical planning can include reorienting bone fragments (if more than one fragment is present) and placing a virtual representation of an implant, prosthesis and/or tool into the 3D image by means of said computer.

In yet another embodiment the method comprises the further step of:

positioning at least one virtual target in or on each virtual anatomical object of a body portion of a patient which is relevant for said surgical operation and at each relevant instrument, tool or implant used during performing the planned surgical procedure by using said computer, said 3D representation of a relevant body portion of a patient and each a 3D representation of said relevant instrument, tool or implant.

Said virtual targets are positioned at distinctive positions on each of the items to be tracked during the planned surgical procedure, which can be bone fragments, implants, tools or the aiming device itself. This step is not needed when the targets (markers) are placed before 3D radiologic imaging.

If the above step can be omitted, the error due to registration of the targets is eliminated (the error that occurs when virtually placing the targets at a more or less significant position on the virtual representation of the bone and reconstructing this exact position during surgery).

In a further embodiment the method further comprises the step of:

determining the position and orientation of each said virtual anatomical objects of a body portion of a patient which is relevant for said surgical operation and of each relevant instrument, tool or implant used during performing the planned surgical procedure according to the planning of the surgical procedure performed under step III) by using said computer.

In again another embodiment the method further comprises the step of:

determining the position and orientation of each object of a body portion of a patient which is relevant for said surgical operation and of each relevant instrument, tool or implant used during performing the planned surgical procedure with regard to the orientations of said targets according to the above step b) by using said computer.

In case of a reposition of bone fragments or performing osteotomies the device according the invention can be attached to the bone fragments or directly to the target acting as a handle for positioning the bone fragments.

When attaching the device to a bone fragment the device can be used as a joystick to manipulate the bone fragment with regard to its position. The final position is achieved by using the target curves projected onto the display of a computer as specified in the above steps b) to f).

The above described method can particularly be used:
for aligning a tool or instrument to a target in a three-dimensional body;
for non-destructive measurement and determination of a desired position of a bore hole to be drilled into a three-dimensional body coaxially to a desired hole axis by aligning an aiming device to said hole axis;
for location and treatment of an implanted cardiac pacemaker;
for treatment of multilayer printed circuit boards; and
for spatial manipulating a three-dimensional body including at least a first and a second target by means of a manipulating device.

In one embodiment the device according to the invention is used for aligning a tool or instrument to a target in a three-dimensional body.

In another embodiment the device according to the invention is used for non-destructive measurement and determination of a desired position of a bore hole to be drilled into a three-dimensional body coaxially to a desired hole axis by aligning said device to said hole axis.

In yet another embodiment the device according to the invention is used for location and treatment of an implanted cardiac pacemaker.

In a further embodiment the device according to the invention is used for treatment of multilayer printed circuit boards.

In still a further embodiment the device according to the invention is used for spatial manipulating a three-dimensional body including at least one target by means of a manipulating device.

In another embodiment the device according to the invention is used for inserting screws or guide-wires into a bone or other objects.

In again another embodiment the device according to the invention is used for repositioning of bone fragments according to surgical planning.

In a further embodiment the device according to the invention is used for achieving an anatomical reconstruction after correction osteotomies according to surgical planning.

A BRIEF DESCRIPTION OF THE DRAWINGS

Several embodiments of the invention will be described in the following by way of example and with reference to the accompanying drawings in which:

FIG. 5 is a schematic sketch of the simulation of the device according to the invention and the projections of the target curves used in an embodiment of the method for positioning the device, instrument or tool with respect to a three-dimensional body;

FIG. 6 illustrates a perspective view of a computer used in the method according to the invention;

Figure 1:
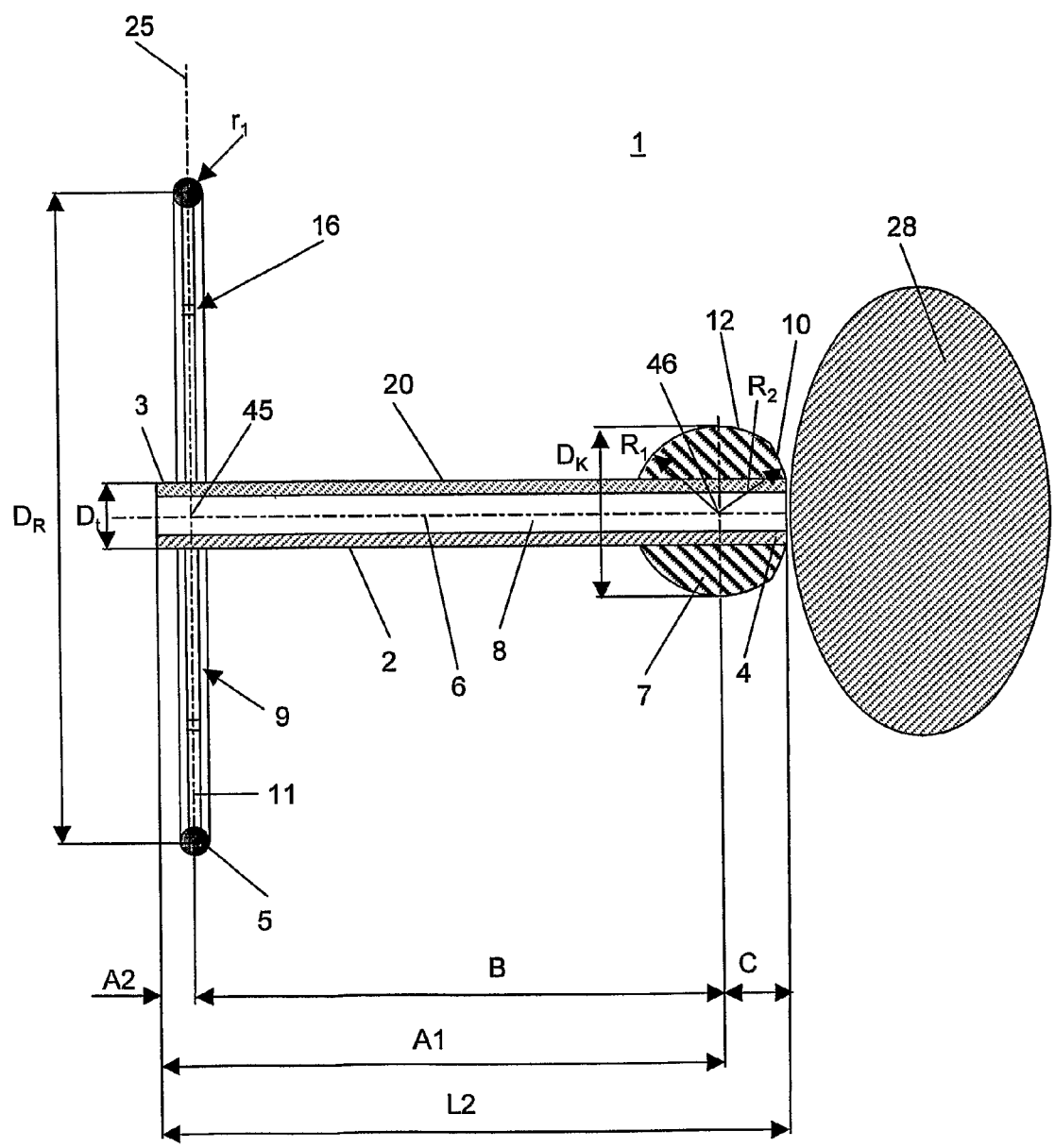
FIG. 1 illustrates a longitudinal section of an embodiment of the device according to the invention.
Figure 2:
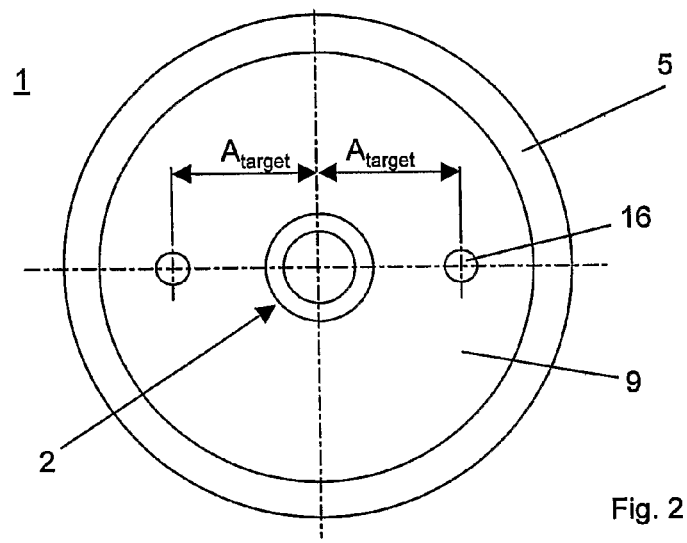
FIG. 2 illustrates a side view on the embodiment of FIG. 1.

FIGS. 1 and 2 illustrate an embodiment of the device which is exemplarily configured as an aiming device 1. Said aiming device 1 essentially comprises a rod shaped member 2 with a central axis 6, an external diameter $D_t$, a radiopaque first targeting element 7 with a diameter $D_K$ fixed to said rod shaped member 2 and a radiopaque second targeting element 5 with circular central line 11 having a diameter $D_R > D_t$ and defining a plane perpendicular to said central axis 6. Further, said rod shaped member 2 includes a central through bore 8 for guiding said drill bit, a rear end 3 and a front end 4 both transverse to the central axis 6. Said first targeting element 7 is fixed to said rod shaped member 2 close to said front end 4 with its center 46 at a distance C>0 thereto and concentrically to said central axis 6.

Said second targeting element 5 is coupled to said rod shaped member 2 concentrically to said central axis 6 such that said plane defined by said circular central line 11 is at a distance A2 measured from said rear end 3 towards said front end 4. Further, said second targeting element 5 is fixedly attached to said rod shaped member 2 by radiolucent means 9, which are realized in the present embodiment by means of a radiolucent disc radially extending between the peripheral surface 20 of said rod shaped member 2 and said second targeting element 5. Further, said second targeting element 5 is configured as a torus obtained by rotating a circle of radius $r_1$ about said central axis 6 of said rod shaped member 2 with said centre of the circle of radius $r_1$ at a distance $D_R/2$ from said central axis 6.

Said first targeting element 7 has a spherical portion 12 directed towards said rear end 3 of said rod shaped member 2. Said spherical portion 12 has a radius of curvature R1 the centre of which coincides with the center 46 of said first targeting element 7. Further, said spherical portion 12 is limited by the external surface 20 of said rod shaped member 2 towards said rear end 3 of said rod shaped member 2 and extends over the median plane of a sphere with radius R1 which is orthogonal to said central axis 6 of said rod shaped member 2. Toward said front end 4 said spherical portion 12 is limited by a front portion 10 with a radius of curvature R2 which is greater than said radius of curvature R1 of said spherical portion 12.

Further, said first targeting element 7 is fixed to the peripheral surface 20 of said rod shaped member 2 concentrically to said central axis 6 with its center 46 at a distance A1 measured from said rear end 3 towards said front end 4 and at a distance B measured from said plane defined by said circular central line 11. Further, the diameters $D_t$ of the rod shaped member 2, $D_K$ of the spherical first targeting element 7 and $D_R$ of the second targeting element are selected in such manner that $D_t < D_K < D_R$.

Optionally, said aiming device 1 can comprise two cylindrical or prismatical targets 16. Said two cylindrical or prismatical targets 16 can be located in said radiolucent disc parallel to each other and at an identical distance $A_{Target}$ to said central axis 6 of said rod shaped member 2.

Figure 3:
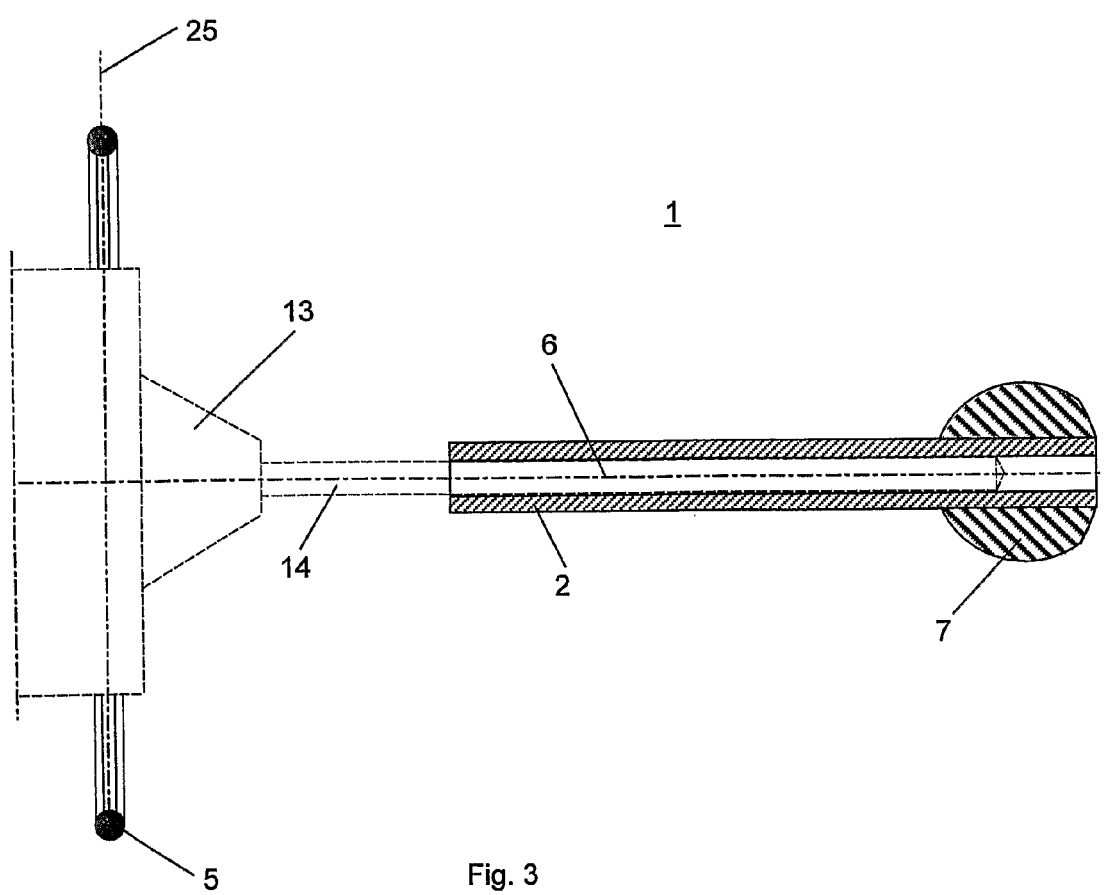
FIG. 3 illustrates a longitudinal section of another embodiment of the device according to the invention.

FIG. 3 illustrates another embodiment of said aiming device 1 which differs from the embodiment of FIGS. 1 and 2 only therein that said second targeting element 5 is not fixed to said rod shaped member 2 but is joinable to a surgical instrument, particularly to a drilling device which is displaceable parallel to said central axis 6 with respect to said rod shaped member 2 so that said second targeting element 5 remains coaxial to said central axis 6.

Figure 4:
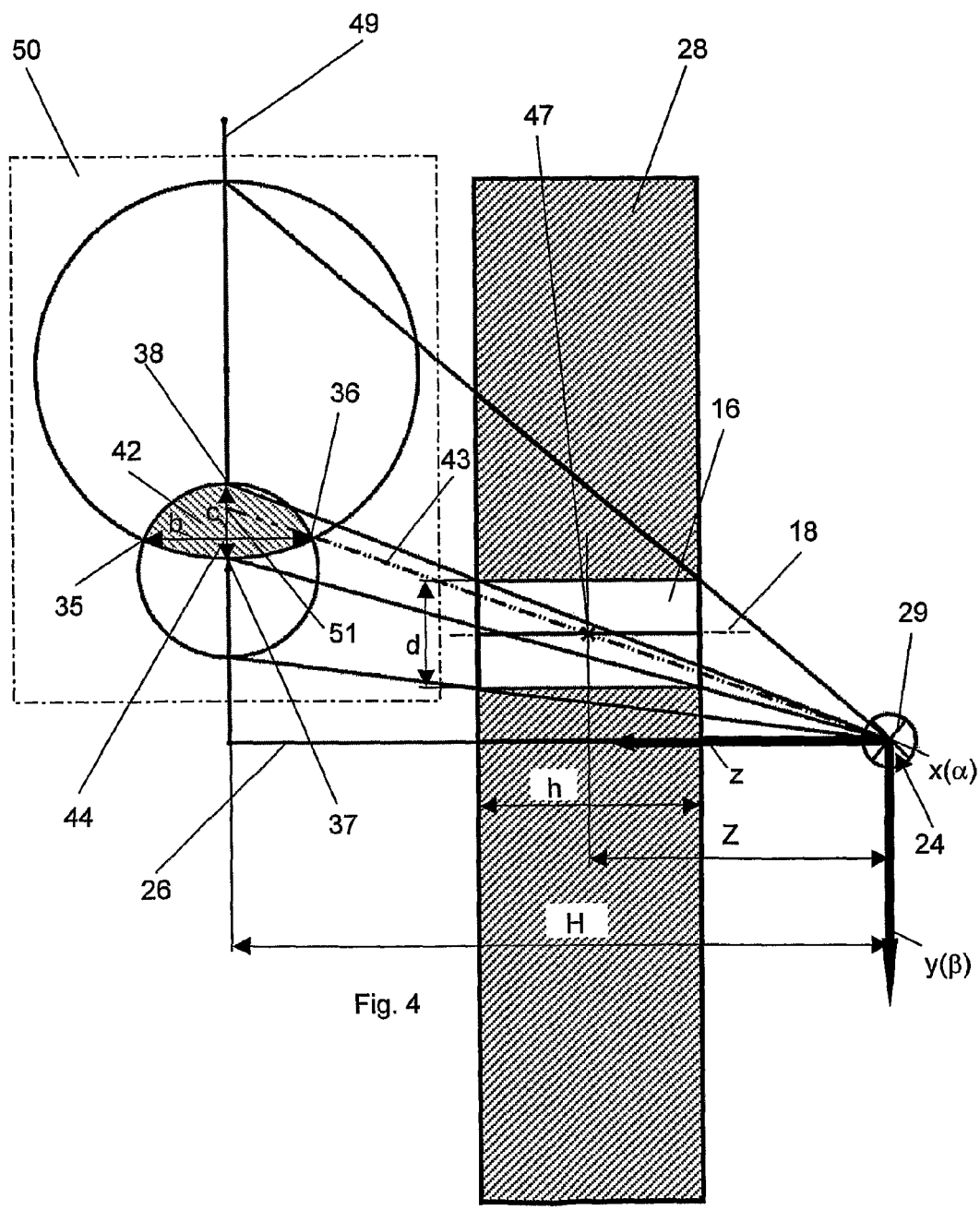
FIG. 4 is a schematic sketch of a central perspective of a circular cylindrical target in a three-dimensional body.

FIG. 4 illustrates the steps performed for determining the position of a circular cylindrical target 16 in a three-dimensional body 28. Said circular cylindrical target 16 has a lower density than the surrounding material of said three-dimensional body 28, a longitudinal axis 18, a diameter d, a height h and a centre 47. In particular said steps comprise:

A) acquiring one single image 50 (schematically illustrated in the drawing plane of FIG. 6) with a lens-shaped projection 42 of said target 16 by means of an image acquisition device including an energy emitting source 29 with a central ray 26 and a receiving device with an image sensor which is connected to a computer 32 with a display 33. The angulation range between the central ray 26 and the longitudinal axis 18 of target 16 is restricted in a way that a projection 42 of the target 16 must be visible on the image 50;

B) determining the position and orientation of said target 16 from said single image 50 using a numerical procedure executed with said computer 32, wherein said numerical procedure essentially comprises the steps of:

a) automatic detection of said lens-shaped projection 42 of said target 16 in said image 50 and determination of the projection points of the two points of intersection 35, 36 and the first and second apex 37, 38 of said lens-shaped projection 42 of said target 16;

b) generating a virtual geometric representation of said target 16, with said diameter d, said longitudinal axis 18, said centre 47 and said height h;

c) determining virtual projection points representing said two points of intersection 35, 36 and said first and second apex 37, 38 using said virtual geometric representation of said target 16;

d) iterative determination of the position and angular orientation of said target 16 by matching said virtual projection points of said virtual geometric representation of said target 16 with said two points of intersection 35, 36 and said first and second apex 37, 38, wherein said target 16 has three degrees of freedom:

a position Z on the z-axis of a global system of coordinates 24 measured between the centre of said energy emitting source 29 and said centre 47. Said virtual geometric representation of said target 16 can slide along the centre line 43 determined by the centre of projection 44 and the centre of said energy emitting source 29. Said centre of projection 44 is an approximation of the centre-line projection 51 for h/H→0. The coordinates x and y of the target 16 are depending on Z and the centre line 43. Therefore, one cylindrical target 16 determines five degrees of freedom but the algorithm needs only three degrees of freedom;

an angle α between said longitudinal axis 18 and said centre line 43 measured in the y-z plane of said global system of coordinates 24 which is fix with respect to said image acquisition device 25; and an angle β between said longitudinal axis 18 and said centre line 43 measured in the x-z plane of said global system of coordinates 24.

Examples when Using One Rotational Symmetrical, e.g. Cylindrical Target Only, Mainly Drilling, Tapping and Screw Insertion Procedures (5 Degrees of Freedom):

guide any type of tool in a predetermined direction with respect to a work piece or other object for further machining or processing of said work piece or other object;

measurement of alignment of a printed circuit board and register subsequent drilling of a bore hole;

fixation, e.g. interlocking of a shaft of an endoprosthesis provided with screw holes by means of screws (e.g. shaft of femur component);

measurement of layer displacement in a multilayer board or panel for e.g. quality control; and measurement of distortion and/or rotation of a single or multi-layer work piece or other object in order to recover a desired shape or orientation or in order to align a robotic arm in e.g. a robotic assembly system;

The work piece or other object could be fixed to a support table of e.g. a CNC-machine (computerized numerical control—machine) such being mechanically constraint.

Examples when Using One Non Rotational Symmetrical Target or Two or More Targets (6 Degrees of Freedom):

determination of the alignment of objects that may not be mechanically constraint in a predetermined location or angular orientation, for example locating and manipulating of a cardiac pacemaker, e.g. tightening or loosening of a screw; and handling or manipulating of a work piece or other object with respect to exact knowledge of its position and orientation.

The above mentioned numerical procedure includes a numerical approach for calculating the position of said target 16 and is based on the following mathematical relationships:

Numerical Approach (for Circular Cylindrical Targets):

The procedure relates to the mathematical condition that the projection of an image acquisition device 25 is based on an idealized central perspective. A punctiform x-ray source used as energy emitting source 29 sends rays from an origin of known distance H to the projection plane 49.

The procedure incorporates the following fundamental steps:

1. Automatic detection of the lens-shaped projection 42 of said target 16 in said image 50 and determination of significant landmarks, i.e. said two points of intersection 35, 36 and the first and second apex 37, 38 of the lens-shaped projection 42 of said target 16 by use of image processing algorithms. Assumption: With h/H→0 the centre-line projection 51 approximates to the centre of projection 44.

2. Simulation of a virtual geometric representation of said target 16 and of virtual projection points corresponding to the above significant landmarks. Iterative determination of the angular orientation and position of said virtual geometric representation by means of a numerical optimization routine; and 3. Simulation of a virtual geometric representation of said aiming device 1 and projection of target curves 17, 22 (targeting ellipses) into the image 50.

Iterative Determination of the Orientation of the Virtual Geometric Representation A virtual geometric representation of said target 16 is generated with the known attributes d (diameter) and h (length). The virtual geometric representation of said target 16 has one translational degree of freedom. It can slide along the central line 43, determined by the centre of projection 44 and the centre of said energy emitting source 29. Sliding position is controlled by Z (FIG. 4). With further two rotational degrees of freedom ($\alpha$, $\beta$) the position of said virtual geometric representation of said target 16 is fully constrained.

Four virtual projection points representing said two points of intersection 35, 36 and said first and second apex 37, 38 are derived from the orientation of said virtual geometric representation of said target 16.

A numerical optimization routine (here least square error minimization) is used to find a global minimum for the deviations between said significant landmarks and the corresponding virtual projection points using three degrees of freedom (DOF) ($\alpha$, $\beta$, Z) in order to carry out the optimized orientation of said virtual geometric representation of said target 16. Due to the asymmetry of the lens shaped projection (segments b and c appear asymmetrically, due to the nature of a central projection) it is possible to calculate a unique solution for the orientation of the target from a single image.

Target Curves (e.g. Ellipses)

With determined orientation of the virtual geometric representation of said target 16 ($\alpha$, $\beta$, Z) the device comprising a first and a second targeting element 7, 5 is mathematically modelled.

The virtual geometric representation of said device with said first and second targeting elements 7, 5 is positioned and oriented with respect to the virtual geometric representation of said target 16.

The projections of the first and second targeting element 7, 5 (target curves, i.e. target ellipses) are visualized in the x-ray image 50 for subsequent targeting.

In the special embodiment illustrated by FIGS. 5 and 6 said device is an aiming device 1 comprising coaxially arranged a spherical first targeting element 7 and an annular second targeting element 5 with the dimensions $D_K$, $D_R$, B, C. Further, the virtual geometric representation of said aiming device 1 is coaxially oriented to the virtual geometric representation of said target 16 and positioned at a distance E from the centre 47 of said target 16 (FIG. 5).

Figure 7:
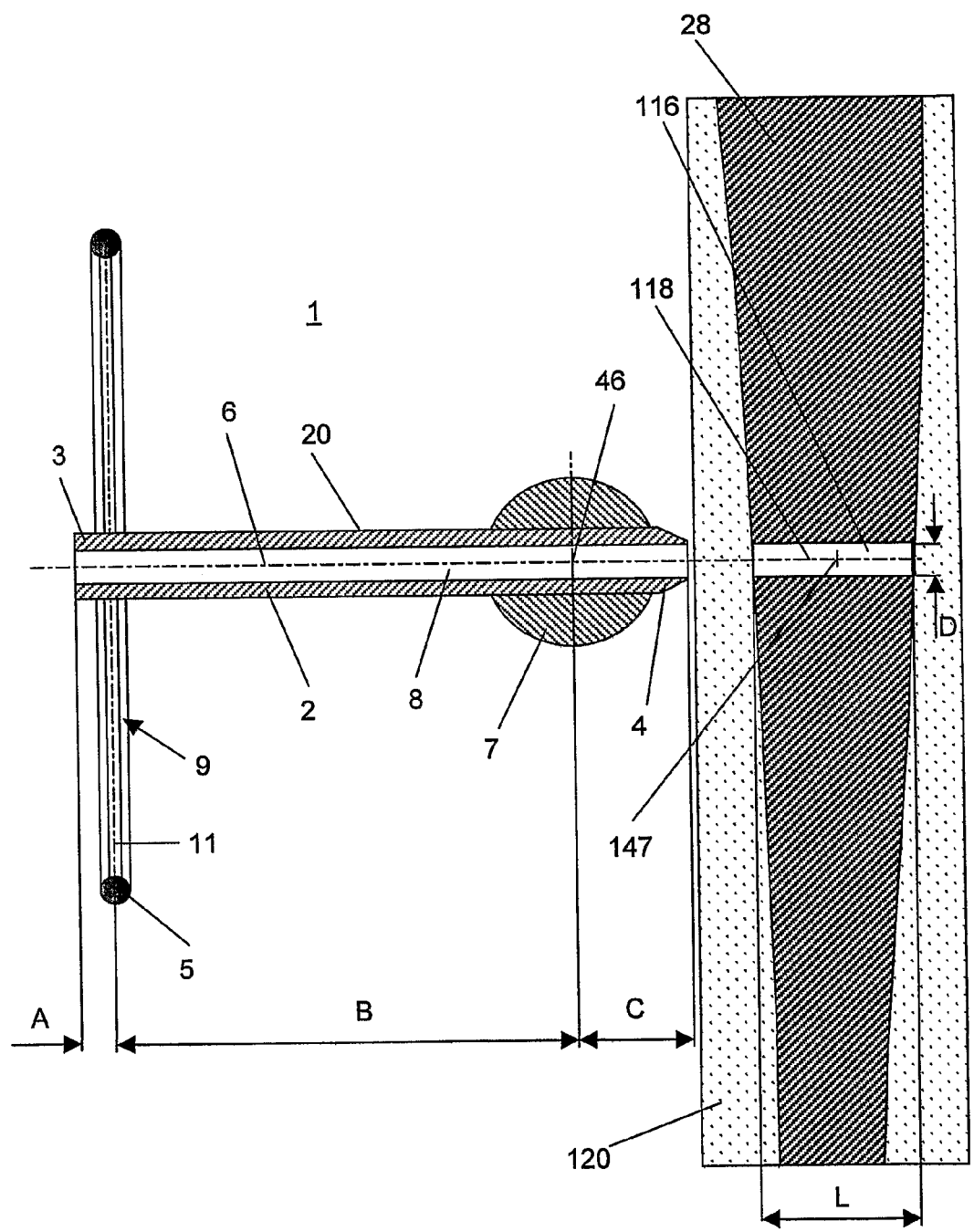
FIG. 7 illustrates a longitudinal section of a further embodiment of the device according to the invention.

Exemplarily, with reference to FIG. 7 the method for positioning a device is described for positioning an aiming device 1 with regard to a through hole 116 in an endoprosthesis representing said three-dimensional body 28, wherein said through hole 116 has a hole axis 118, a bore diameter D and a bore centre 147.

In the following description:
said endoprosthesis represents the three-dimensional body 28;
said through hole 116 represents the circular cylindrical target 16 wherein said hole axis 118 represents with said longitudinal axis 18 of said target 16;
said diameter d of said target 16 is represented by the bore diameter D of said through hole 116, said height h of said target 16 is represented by the length L of said through hole 116 and said centre 47 of said target 16 is represented by the bore centre 147 of said through hole 116; and
the aiming means attached to said aiming device 1 are realized by said spherical first targeting element 7 and said annular second targeting element 5.

On the above basis said through hole 116 with said hole axis 118 is used in said numerical procedure to generate said virtual geometric representation of said target 16 with said diameter d, said longitudinal axis 18, said height h and said centre 47.

The aiming device 1 used in the embodiment here differs from the aiming device of FIG. 1 only therein that said first targeting element 7 is spherically configured with a diameter $D_K$.

Firstly, the step of acquiring one single image 50 with a projection 42 of said through hole 116 by means of an image acquisition device with a projection plane 49 is performed.

Secondly, the position and angular orientation of said through hole 116 is determined by applying said numerical procedure using said single image 50 as described under FIG. 4.

Then, as illustrated in FIGS. 5 and 6 said aiming device 1 is positioned by performing the further steps of:

1) establishing a virtual geometrical representation of said aiming device 1 coaxial to said longitudinal axis 18 of said through hole 116 and positioned with said front end 4 of said aiming device 1 at a distance E to said centre 147 by means of said computer 32;

2) determining the virtual position and angular orientation of said spherical first targeting element 7 and said annular second targeting element 5 attached to said aiming device 1 using said virtual geometrical representation of said aiming device 1;

3) depicting a first target curve 17 on said display 33 by means of said computer 32; said first targeting curve 17 representing a virtual projection of said spherical first targeting element 7 on said projection plane 49;

4) depicting a second target curve 22 on said display 33 by means of said computer 32; said second targeting curve 22 representing a virtual projection of said annular second targeting element 5 on said projection plane 49; and 5) positioning said aiming device 1 by aligning said spherical first targeting element 7 with said first targeting curve 17 and by subsequently aligning said circular central line 11 of said annular second targeting element 5 with said second targeting curve 22 using an image acquisition device 25; wherein i) said positioning of said aiming device 1 is performed by firstly manually aligning said spherical first targeting element 7 of said aiming device 1 with said first targeting curve 17 by translational movement of said aiming device 1; and ii) by secondly aligning said circular central line 11 of said annular second targeting element 5 with said second targeting curve 22 by rotational movement of the aiming device 1.

When said aiming device 1 is correctly positioned with regard to said through hole 116 a hole is drilled in the bone 120 surrounding said endoprosthesis.

After drilling the hole in the bone 120 surrounding said endoprosthesis coaxially to said hole axis 118 of said through hole 116 an interlocking means, e.g. a bone screw could be advanced through the through hole 116 such locking said endoprosthesis with respect to said bone 120.

In order to operate said aiming device 1 during drilling of bore holes through a material surrounding said three-dimensional body 28 coaxially to said hole axis 118 of said through hole 116 in said three-dimensional body 28 the aiming device 1 comprises a handle (not shown).

While various descriptions of the present invention are described above, it should be understood that the various features can be used singly or in any combination thereof. The scope of the present invention is accordingly defined as set forth in the appended claims.

The invention claimed is:

1. A device for guiding an instrument, tool or implant with respect to a three-dimensional body, the device comprising:
   a rod shaped member with a central axis, a rear end, a front end and a length L2;
   a radiopaque first targeting element having a first center, wherein said first targeting element is affixed directly on said rod shaped member coaxially to said central axis with said first center at a distance A1>0 from said rear end; and
   a radiopaque second targeting element having a second center, wherein said second targeting element is fixed with respect to said rod shaped member coaxially to said central axis with said second center at a distance A2<A1 from said rear end;
   wherein:
   said first targeting element has a first spherical surface portion directed toward said rear end of said rod shaped member and limited by an external surface of said rod shaped member, and a second spherical surface portion directed toward said front end of end of said rod shaped member,
   a cross-sectional area of said first targeting element orthogonal to said central axis and containing said first center has a circular periphery with a diameter $D_K$ of no less than 10 mm;
   said second targeting element is annular and has a circular central line with a diameter $D_R > D_K$, said circular central line lying in a plane perpendicular to said central axis, said second targeting element being arranged in such manner that its circular central line is concentric with said central axis; and
   said second targeting element is fixedly attached to said rod shaped member by a radiolucent structure.

2. The device according to claim 1, wherein the first spherical portion has a radius of curvature R1 and said second spherical portion has a radius of curvature R2 which is equal or greater than R1.

3. The device according to claim 1, wherein said device is an aiming device and wherein said rod shaped member is a tubular member with an external diameter $D_t$ and a central through bore for guiding the instrument, tool or implant with respect to the three-dimensional body.

4. The device according to claim 1, wherein said device comprises at least two cylindrical or prismatical targets integrated in said radiolucent structure, wherein said at least two cylindrical or prismatical targets are arranged parallel to each other and at an identical distance $A_{Target}$ from said central axis of said rod shaped member.

5. A method for positioning a device according to claim 1 in a desired position with respect to a three-dimensional body after having determined the position of at least one cylindrical or prismatical target in said three-dimensional body, wherein said target has a different density than the surrounding material of said three-dimensional body, a longitudinal axis, a height h and a center, said method comprising the steps of:
   a) acquiring one single image using an image acquisition device with a projection of said target into a projection plane of said image acquisition device;
   b) determining the position and angular orientation of said target with respect to a global system of coordinates fixed to said image acquisition device using a numerical procedure using said single image and by using a computer with a display;
   c) establishing a virtual geometrical representation of the device in the desired position with respect to said target or three-dimensional body using said computer;
   d) depicting a first target curve on said display using said computer, wherein said first target curve represents a virtual projection of said first targeting element of said virtual geometrical representation of said device on said projection plane;
   e) depicting a second target curve on said display using said computer; wherein said second target curve represents a virtual projection of said second targeting element of said virtual geometrical representation of said device on said projection plane; and
   f) positioning said device according to claim 1 by aligning said first targeting element with said first target curve and by aligning said second targeting element with said second target curve using the image acquisition device.

6. The method according to claim 5, wherein said positioning of said device is performed manually.

7. The method according to claim 5, wherein said positioning of said device is performed by firstly aligning said first targeting element with said first targeting curve by translational movement of said device and by secondly aligning said second targeting element with said second targeting curve by rotational movement of said device.

8. The method according to claim 5, wherein said image acquisition device includes an energy emitting source allowing an approximation as a punctiform energy source and with a central ray at a known position with regard to said image and wherein said target is circular cylindrical and that upon acquiring said single image the angulation range between the central ray and the longitudinal axis of said target is restricted in a way that a lens-shaped projection of said target is visible on said image, said lens-shaped projection having two points of intersection and first and second apexes.

9. The method according to claim 8, wherein said numerical procedure in step b) comprises the steps of:
   i) automatic detection of the lens-shaped projection of said target in said image and determination of the two points of intersection and the first and second apexes of said lens-shaped projection of said target;
   ii) generating a virtual geometric representation of said target with said diameter d, said longitudinal axis, said center and said height h;
   iii) determining the virtual projection points representing said two points of intersection and said first and second apex using said virtual geometric representation of said target; and iv) iterative determination of the position and orientation of said target by matching said virtual projection points of said virtual geometric representation of said target with said two points of intersection and said first and second apex.

10. The method according to claim 5, further comprising the steps of:
   determining the position of at least two cylindrical targets in said three-dimensional body, wherein said targets are arranged with known position and orientation relative to each other; and
   determining the position and angular orientation of said three-dimensional body with respect to a fixed system of coordinates using said position and angular orientation of said at least two cylindrical targets using said computer.

11. The method according to claim 5 further comprising the additional steps of:
   I) fixing the at least one target in or on each object which is relevant for a surgical procedure;
   II) establishing a 3D representation of a relevant body portion of a patient using a standard medical acquisition device;
   III) planning of the surgical procedure to be performed at said relevant body portion using a computer and said 3D representation of the relevant body portion; and
   IV) performing the planned surgical procedure using said device according to claim 1 and said computer.

12. The method according to claim 11, wherein said step of I) fixing at least one target in or on each object which is relevant for said surgical procedure is performed before step II) is performed.

13. The method according to claim 11, wherein said step of I) fixing at least one target in or on each object which is relevant for said surgical procedure is performed before step III) is performed.

14. The method according to claim 11, wherein said step of I) fixing at least one target in or on each object which is relevant for said surgical procedure is performed after steps II) and III) are performed but before step a) is performed.

15. The method according to claim 11, wherein if two or more targets are fixed in or on objects which are relevant for the surgical procedure and not all targets of all objects are visible in said single image, step a) of claim 9 is repeated for further objects until the projection of all targets of each object are visible in one of said images.

16. The method according to claim 11, further comprising the step of: positioning at least one virtual target in or on each virtual anatomical object of a body portion of a patient which is relevant for said surgical procedure and at each relevant instrument, tool or implant used during performing the planned surgical procedure by using said computer, said 3D representation of a relevant body portion of a patient and each a 3D representation of said relevant instrument, tool or implant.

17. The method according to claim 16, further comprising the step of: determining the position and orientation of each said virtual anatomical objects of a body portion of a patient which is relevant for said surgical procedure and of each relevant instrument, tool or implant used during performing the planned surgical procedure according to the planning of the surgical procedure performed under step III) by using said computer.

18. The method according to claim 17, further comprising the step of: determining the position and orientation of each object of a body portion of a patient which is relevant for said surgical procedure and of each relevant instrument, tool or implant used during performing the planned surgical procedure with regard to the orientations of said targets according to step b) by using said computer.

* * * * *